United States Patent [19]

Herlihy

[11] Patent Number: 4,518,691

[45] Date of Patent: May 21, 1985

[54] IN VITRO ENZYMATIC PROCESS FOR PREPARING GLUCURONIDES OF ESTER-CONTAINING ANTICHOLINERGICS

[75] Inventor: Walter C. Herlihy, Cambridge, Mass.

[73] Assignee: Repligen Corporation, Cambridge, Mass.

[21] Appl. No.: 607,348

[22] Filed: May 4, 1984

Related U.S. Application Data

[62] Division of Ser. No. 398,212, Jul. 14, 1982, Pat. No. 4,471,111.

[51] Int. Cl.³ .................. C12P 19/44; C07H 15/18
[52] U.S. Cl. .................... 435/74; 536/17.3; 536/17.4; 536/18.2; 546/268
[58] Field of Search .............. 435/74, 77; 536/17.3, 536/17.4, 18.2; 546/268

[56] References Cited

U.S. PATENT DOCUMENTS 3,624,200 11/1971 Moffett ........................ 424/65
3,767,786 10/1973 MacMillan ................... 424/65
3,855,067 12/1974 Bellavita ..................... 435/74
4,129,721 12/1978 Michel et al. ............... 435/77

Primary Examiner—Johnnie R. Brown
Attorney, Agent, or Firm—Roman Saliwanchik

[57] ABSTRACT

An in vitro enzymatic process which efficiently converts ester-containing anticholinergics having a primary alcohol to their corresponding novel O-glucuronic acid derivatives. These novel glucuronides are useful as antiperspirants.

14 Claims, No Drawings

IN VITRO ENZYMATIC PROCESS FOR PREPARING GLUCURONIDES OF ESTER-CONTAINING ANTICHOLINERGICS

The present application is a divisional application of co-pending application Ser. No. 398,212, filed on July 14, 1982, now U.S. Pat. No. 4,471,111.

DESCRIPTION

BACKGROUND OF THE INVENTION

Anticholinergic compounds are well known for their property of controlling perspiration. U.S. Pat. Nos. 3,624,200 and 3,767,786 disclose and claim processes for controlling perspiration with scopolamine esters.

It is well known that anticholinergic compounds have a mydriatic effect. This mydriatic effect, though desirable in conjunction with an eye examination by an eye doctor, is an undesirable property for an antiperspirant because an accidental transfer of an anticholinergic antiperspirant to the eye can represent a significant safety problem.

As exemplified by the above-mentioned U.S. patents, the predominant anticholinergics made for antiperspirant use are scopolamine and its esters. Though the efficacy of scopolamine and its esters was demonstrated over twenty years ago, it is apparent that these compounds have not achieved widespread use as antiperspirants. This lack of use may be related to the mydriatic property referred to above, and, additionally, to the fact that ester-containing anticholinergics such as scopolamine may be cleaved by esterase activity in human perspiration, thus rendering the anticholinergic ineffective as an antiperspirant.

The problems of esterase inactivation and mydriasis, discussed above, have been overcome by the novel glucuronide compounds of the subject invention which are made by a novel in vitro enzymatic process.

The preparation of β-glucuronides has been carried out by a number of different techniques. Chemical synthesis typically involves condensation of a suitable protected aglycon with an alkyl (2,3,4-tri-O-acetyl-α-D-glucopyranosyl halide) glucuronate followed by deprotection of the glucuronide and aglycon (Ando, K., Suzuki, S., and Arita, M. [1970] *J. Antibiotics* 23, 408; Sarett, L. H., Strachan, R. G., and Hirschmass, R. F. [1966] U.S. Pat. No. 3,240,777). A second approach involves feeding large amounts of the aglycon to animals, collecting their urine and isolating the glucuronide (Hornke, I., Fehlhaber, H. W., Uihlein, M. [1979] U.S. Pat. No. 4,153,697). Alternatively, the animal can be sacrificed and the bile isolated from its gall bladder, from which the glucuronide is purified (DeLuca, H. F., Schnoes, H. K., and LeVan, L. W. [1981] U.S. Pat. No. 4,292,250). This in vivo synthesis is catalyzed by the class of enzymes known as uridine diphosphoglucuronyl transferases. In vitro use of this enzyme to produce various β-glucuronides has been reported; for example, a phenolic compound has been glucuronidated (Johnson, D. B., Swanson, M. J., Barker, C. W., Fanska, C. B., and Murrill, E. E. [1979] *Prep. Biochem.* 9, 391).

An in vitro enzymatic process for the synthesis of β-glucuronides has several advantages over prior art chemical synthesis or animal feeding methods. Chemical synthesis requires a minimum of four steps: (1) protection of all the nucleophilic groups in the aglycon except the one involved in the glycosidic linkage, (2) preparation of a suitably protected reactive derivative of D-glucuronic acid, e.g., methyl (2,3,4-tri-O-acetyl-β-D-glucopyranosyl halide) glucuronate, (3) condensation, and (4) deprotection. Complications arise if the aglycon contains functional groups sensitive to the conditions of deprotection. For example, aglycons containing esters or other alkali-sensitive linkages can be hydrolyzed during the saponification of the methyl and acetyl protecting groups. In contrast, an in vitro enzymatic process involves a single step condensation between a readily available cofactor and the aglycon.

The animal feeding approach to making β-glucuronides also has several disadvantages as compared to an in vitro enzymatic method. The most significant disadvantage is that stringent purification is required. Other disadvantages are the inconvenience of maintaining animals, and other metabolic pathways including hydroxylation, alkylation, and sulfation can compete with glucuronidation, thus resulting in low yields of the desired product.

The subject enzymatic process for the glucuronidation of ester-containing anticholinergics was unexpectedly successful in view of the fact that prior attempts to glucuronidate the ester-containing anticholinergic scopolamine were unsuccessful. The subject invention process is the first known in vitro enzymatic process for preparing glucuronides of ester-containing anticholinergics having a primary alcoho.

BRIEF SUMMARY OF THE INVENTION

Novel glucuronides of ester-containing anticholinergics are prepared by first removing all or substantially all of the esterase activity from liver microsomes. These esterases are removed since they will hydrolyze the aglycon and/or its glucuronic acid derivative. This operation can be done by washing the liver microsomes in a suitable buffer, as described herein, or by other equivalent washing means known to persons in this art. Advantageously, an esterase inhibitor can be used to supplement the washing of the microsomes. For example, a competitive inhibitor of the esterases such as lysine ethyl ester, and the like, or a suicide substrate such as phenylmethylsulfonyl fluoride, and the like, can be used. The thus obtained liver microsomes are then incubated for a sufficient length of time with the following:

(1) a suitable buffer to maintain the pH at about 7 to about 8.5;

(2) an ester-containing anticholinergic having a primary alcohol; and (3) UDPGA (uridine 5'-diphosphoglucuronic acid).

A sufficient length of time for incubation is that which allows the conjugation of the aglycon with glucuronic acid.

DETAILED DESCRIPTION OF THE INVENTION

The in vitro enzymatic process of the subject invention accomplishes, for the first time, the glucuronidation of ester-containing anticholinergics having a primary alcohol to produce novel O-glucuronides.

An anticholinergic compound is well known to persons skilled in the art. Such a compound inhibits the action of a chemical mediator, acetylcholine, which activates sweat glands in humans.

Ester-containing anticholinergics having a primary alcohol are a well-known class of compounds. Member of this class are scopolamine, hyoscyamine, atropine, and the like.

Heretofore, attempts to prepare glucuronides of ester-containing anticholinergics were unsuccessful. It is now realized that this lack of success was caused by the esterase activity of the liver microsomes. The process of the subject invention overcomes this problem and, thus, enables the preparation of glucuronides of ester-containing anticholinergics by an in vitro enzymatic process. Surprisingly, ester-containing anticholinergics having a secondary or tertiary alcohol were not O-glucuronidated by the subject process.

The glucuronides of ester-containing anticholinergics are useful as antiperspirants. These glucuronides do not demonstrate the undesirable mydriatic property of the ester-containing anticholinergics. This then overcomes one of the problems, discussed above, in the use of ester-containing anticholinergics as antiperspirants.

A further advantageous property of the novel glucuronides of the subject invention is that their antiperspirant activity is not destroyed by the esterase activity in human perspiration, at least not to the extent that it is destroyed in the non-glucuronidated compounds. On the contrary, the glucuronides of the subject invention exhibit a prolonged antiperspirant effect which is considered to be a most advantageous property. For example, scopolamine is completely degraded after a two-hour incubation in a 4 mg/ml suspension of unwashed transferase, whereas scopolamine O-$\beta$-D-glucuronic acid is stable to a two-hour incubation with 40 mg/ml of unwashed transferase. This shows that the glucuronide is at least 100-fold less susceptible to the esterase. This property of the glucuronides of the subject invention is clearly desirable since the effective control of perspiration requires that the active antiperspirant component be released by glucuronidase (an enzyme known to be present on the skin surface and in the axilla) over a prolonged period of time. Advantageously, the glucuronide is protected from esterase cleavage during this time period.

It has been determined that scopolamine O-$\beta$-D-glucuronic acid is cleaved by $E.$ $coli$ $\beta$-glucuronidase approximately twenty-fold slower than cleavage of the non-ester-containing anticholinergic tropicamide O-$\beta$-D-glucuronic acid. This difference in cleavage rates enables the formulation of an antiperspirant containing a mixture of these compounds to achieve antiperspirant activity early on and for a prolonged period of time. Such a mixture of glucuronides which hydrolyze at different rates also, advantageously, compensates for the well-known differences in $\beta$-glucuronidase activity found in the sweat of different people.

The chromatographic methods described herein are based on reversed phase liquid chromatogrpahy on C-18 silica supports. This technique is well suited for the purification of enzymatically-produced glucuronides of hydrophobic compounds. Unreacted aglycon is much more hydrophobic than the corresponding glucuronide and thus will be well resolved on reversed phase systems. The cofactor, UDP glucuronic acid, and the byproduct, UDP, are both very hydrophilic and will be much less retained than the glucuronide of a hydrophobic compound. Finally, all the solvent systems described are based on NH$_4$OAc, a volatile buffer. Modifications to this system may be necessary in order to purify glucuronides of very hydrophilic compounds. Other reversed phase stationary supports, for example, phenyl silica, C-8 silica, and the like, can be used.

Liver microsomes which can be used in the subject invention can be obtained from animal sources, for example, rabbit, bovine, rat, and the like.

The temperature of incubation in the enzymatic step can be from about 20° to about 45° C.

The enzymatic reaction can be carried out over a pH range of about 7 to about 8.5, with different buffer strengths or with other buffers. For example, 3-((tris-(hydroxymethyl)methyl)amino)propane sulfonic acid (Calbiochem-Behring, La Jolla, CA) can be used in place of tris HCl (pH=8.0).

The glucuronides of the subject invention can be formulated for antiperspirant use by use of well-known ingredients and procedures. For example, the formulations and procedures disclosed in U.S. Pat. Nos. 3,624,200 and 3,767,786 can be used by substituting the glucuronides of the subject invention for the antiperspirant compounds disclosed in these patents.

The following examples are illustrative of the process and products of the invention, but are not to be construed as limiting. All percentages are by weight and all solvent mixture proportions are by volume unless otherwise noted.

EXAMPLE 1

Preparation of scopolamine O-$\beta$-D-glucuronic acid

Four hundred milligrams of a rabbit liver or bovine liver microsomal fraction (Sigma Chemical Co., St. Louis, Mo.), containing uridine 5'-diphosphoglucuronyl transferase is suspended in 20 ml of a 75 mM tris HCl buffer (pH=8.0). The microsomes are suspended by repeatedly drawing the mixture through a pipette tip. The microsomes are then pelleted by centrifugation at 44,000 g for 20 minutes. The supernatant is discarded, the pellet washed a second time, and the pellet resuspended to 10 ml with a 75 mM tris HCl (pH=8.0) solution containing 20 mg scopolamine (Sigma) and 140 mg of sodium uridine 5'-diphosphoglucuronic acid (Sigma). In addition, the reaction mixture contains either 100 mM lysine ethyl ester (Sigma) or 10 $\mu$M phenylmethylsulfonyl fluoride (PMSF) (Sigma) which had been predissolved in a small volume of propanol immediately before addition. After a 20 hour incubation at 37° C., the reaction is terminated by heating the sample for two minutes at 70° C., followed by centrifugation at 44,000 g for 20 minutes. The supernatant is removed and analyzed by high pressure liquid chromatography (HPLC). The yield of desired product is determined to be ~95%.

The HPLC conditions are as follows: a 0.47×25 cm C-18 $\mu$Bondapak column (Waters Associates, Milford, Mass.) is eluted at 2 ml/min. with 0.1% NH$_4$OAc (pH=7.5). After injection of the sample, a linear gradient to 60% methanol is applied to the column over a 20-minute period. The column eluant is monitored with an ultraviolet detector set at 254 nm. Under these conditions the reaction product has a retention time of ~12 minutes, whereas scopolamine has a retention time of ~18 minutes. On the basis of the chemical and spectral data presented below, the product is assigned as scopolamine O-$\beta$-D-glucuronide.

EXAMPLE 2

Preparation of hyoscyamine O-$\beta$-D-glucuronic acid

The reaction conditions are identical to those utilized for scopolamine in Example 1. The concentration of hyoscyamine is 2 mg/ml and the reaction is carried out for 20 hours.

EXAMPLE 3

Isolation of scopolamine O-β-D-glucuronide and hyoscyamine O-β-D-glucuronic acid The glucuronides are isolated with the HPLC system described above. Typically, 25 μl of 1% NH4OAc (pH=7.5) is added to 225 μl of the reaction supernatant, and the entire sample is injected. Larger amounts can be prepared with a preparative chromatography system.

Characterization of scopolamine O-β-D-glucuronic acid

The reaction product (150 μg in 450 μl of 50 mM sodium phosphate, pH=6.8) is treated with 150 Fishman units of E. coli β-glucuronidase (EC 3.2.1.31) at 37° C. for two hours. The compound is quantitatively hydrolyzed by the glucuronidase to product which is indistinguishable by HPLC from the starting material, scopolamine, in the 0.1% NH4OAc (pH=7.5)/methanol solvent system described above. The glucuronidase product is also indistinguishable from scopolamine when chromatographed on C-18 in a second solvent system consisting of 1% triethylammonium acetate (pH=7.0) eluted with a linear gradient to 50% acetonitrile in 25 minutes. Since the chromatographic behavior of scopolamine is markedly affected by pH in the range of pH=5-8, the hydrolysis product is chromatographed in a third solvent system consisting of 0.1% NH4OAc (pH=5.0) eluted with a linear gradient to 50% acetonitrile in 25 minutes and found to be identical to scopolamine. These data indicate that the product contains an intact scopolamine moiety. The known specificity of this enzyme indicates the presence of a glucuronic acid moiety and indicates that the glycosidic linkage has the β configuration.

The ultraviolet spectrum of the reaction product is recorded in 0.05% NH4OAc (pH=7.0) and compared to the spectrum of scopolamine. Both compounds exhibit maxima at 252 nm, 258 nm, and 263.5 nm, and a strong end absorption beginning at ~240 nm, indicating that the glucuronide contains an intact tropic acid moiety.

The molecular weight of the product is determined by fast atom bombardment (FAB) mass spectrometry. The xenon FAB spectrum contained a single ion at m/z=480 (M+H)+, clearly indicating a molecular weight of 479. The exact mass of the (M+H)+ ion is determined by peak matching to be 480.186, which is in excellent agreement with the mass expected for a compound with this elemental composition, 480.187.

Scopolamine O-β-D-glucuronic acid has the following structure:

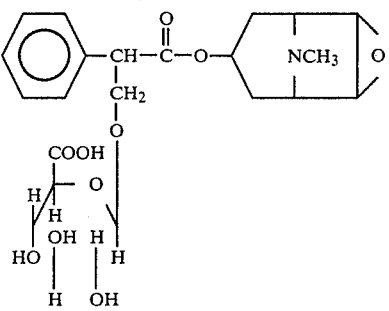

Characterization of hyoscyamine O-β-D-glucuronic acid

The HPLC system used to assay the synthesis of hyoscyamine O-β-D-glucuronic acid consists of a linear gradient from 0.1NH4OAc (pH=5.75) to 60% methanol in twenty minutes. All other parameters are identical to the chromatography described above for scopolamine. Under these conditions the hyoscyamine elutes slightly after scopolamine, and the product of the transferase reaction elutes slightly after scopolamine O-β-D-glucuronic acid, indicating that the expected glucuronide is formed. This product is purified by HPLC. Approximately 40 μg is dissolved in 400 μl of 50 mM sodium phosphate (pH-6.8) containing 1000 U/ml of E. coli β-glucuronidase. Immediately after addition of the enzyme and after a one-hour incubation at 37° C., 50-μl aliquots are removed, heated at 70° C. for 1 minute and analyzed by HPLC. The aglycon released from the glucuronide and hyoscyamine have identical retention in the 0.1% NH4OAc (pH=5.75)/methanol solvent system described above.

Hyoscyamine O-β-D-glucuronic acid has the following structure:

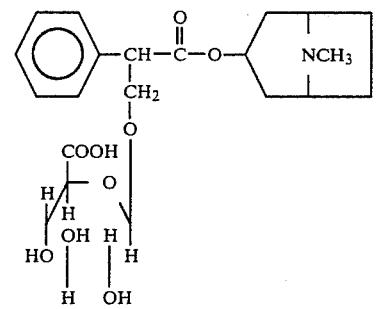

Esterase cleavage of scopolamine and scopolamine O-β-D-glucuronic acid

To 150 μl of 150 mM tris HCl (pH=8.0) solution containing 0.7 mM scopolamine and an equimolar amount of scopolamine O-β-D-glucuronic acid is added 1 mg of unwashed rabbit UDPGA-dependent glucuronyl transferase. Immediately after addition of the enzyme, 50 μl are removed and incubated at 70° C. for 1 minute and centrifuged at 14,000 g for 5 minutes. The supernatant (40 μl) is removed; 4 μl of 1% NH4OAc (pH=7.5) is added, and the sample is analyzed by HPLC using the 0.1% NH4OAc (pH=7.5)/methanol solvent system described above. A second 50-μl sample is prepared and analyzed after a 2-hour incubation at 37° C.

EXAMPLE 4

Upon substituting atropine in Example 2 for hyoscyamine, there is obtained atropine O-β-D-glucuronic acid.

EXAMPLE 5

Upon substituting other ester-containing anticholinergics having a primary alcohol in Example 1 for scopolamine, there are obtained the corresponding ester-containing anticholinergic O-β-D-glucuronic acids.

EXAMPLE 6

Salts with both inorganic and organic bases can be formed with the free acid of the compounds of the subject invention. For example, in addition to the ammonium salt, there also can be formed the sodium, potassium, calcium, and the like, by neutralizing an aqueous solution of the free acid with the corresponding base. The ammonium and other base salts of the compounds of the subject invention are useful in the same manner as the free acid form.

I claim:

1. An in vitro enzymatic process for preparing the O-β-D-glucuronic acid of an ester-containing anticholinergic compound having a primary alcohol which comprises:
   (a) substantially removing esterases from liver microsomes;
   (b) incubating said treated liver microsomes in the presence of:
      (1) a suitable buffer to maintain the pH at about 7 to about 8.5;
      (2) an ester-containing anticholinergic compound having a primary alcohol; and
      (3) uridine 5'-diphosphoglucuronic acid, for a sufficient time to conjugate the aglycon with glucuronic acid, and
   (c) isolating the desired O-β-D-glucuronic acid of said ester-containing anticholinergic compound having a primary alcohol.

2. An in vitro enzymatic process for preparing scopolamine O-β-D-glucuronic acid, according to claim 1, which comprises:
   (a) substantially removing esterases from liver microsomes;
   (b) incubating said treated liver microsomes in the presence of:
      (1) a suitable buffer to maintain the pH at about 7 to about 8.5;
      (2) scopolamine; and
      (3) uridine 5'-diphosphoglucuronic acid, for a sufficient time to conjugate the aglycon with glucuronic acid, and
   (c) isolating scopolamine O-β-D-glucuronic acid.

3. An in vitro enzymatic process for preparing hyoscyamine O-β-D-glucuronic acid, according to claim 1, which comprises:
   (a) substantially removing esterases from liver microsomes;
   (b) incubating said treated liver microsomes in the presence of:
      (1) a suitable buffer to maintain the pH at about 7 to about 8.5;
      (2) hyoscyamine; and
      (3) uridine 5'-diphosphoglucuronic acid, for a sufficient time to conjugate the aglycon with glucuronic acid, and
   (c) isolating hyoscyamine O-β-D-glucuronic acid.

4. A process, according to claim 1, wherein the esterases are removed from the liver microsomes by suspending said liver microsomes containing uridine 5'-diphosphoglucuronyl transferase in a suitable buffer at about pH 8.0, agitating, and pelleting the mixture.

5. A process, according to claim 1, wherein the incubation temperature is from about 20° to about 45° C.

6. An in vitro enzymatic process for preparing the O-β-D-glucuronic acid of an ester-containing anticholinergic compound having a primary alcohol which comprises:
   (a) substantially removing esterases from liver microsomes;
   (b) incubating said treated liver microsomes in the presence of:
      (1) a suitable buffer to maintain the pH at about 7 to about 8.5;
      (2) an ester-containing anticholinergic having a primary alcohol;
      (3) uridine 5'-diphosphoglucuronic acid; and
      (4) a selective residual esterase inhibitor, and
   (c) isolating the desired O-β-D-glucuronic acid of said ester-containing anticholinergic compound having a primary alcohol.

7. A process, according to claim 6, wherein said selective residual esterase inhibitor is a competitive inhibitor of the esterases or a suicide substrate.

8. A process, according to claim 7, wherein said competitive inhibitor is lysine ethyl ester and said suicide substrate is phenylmethylsulfonyl fluoride.

9. An in vitro enzymatic process for preparing scopolamine O-β-D-glucuronic acid, according to claim 6, which comprises:
   (a) substantially removing esterases from liver microsomes;
   (b) incubating said treated liver microsomes in the presence of:
      (1) a suitable buffer to maintain the pH at about 7 to about 8.5;
      (2) scopolamine;
      (3) uridine 5'-diphosphoglucuronic acid and
      (4) a selective residual esterase inhibitor, and
   (c) isolating scopolamine O-β-D-glucuronic acid.

10. A process, according to claim 9, wherein said selective residual esterase inhibitor is a competitive inhibitor of the esterases or a suicide substrate.

11. A process, according to claim 10, wherein said competitive inhibitor is lysine ethyl ester and said suicide substrate is phenylmethylsulfonyl fluroride.

12. An in vitro enzymatic process for preparing hyoscyamine O-β-D-glucuronic acid, according to claim 6, which comprises:
   (a) substantially removing esterases from liver microsomes;
   (b) incubating said treated liver microsomes in the presence of:
      (1) a suitable buffer to maintain the pH at about 7 to about 8.5;
      (2) hyoscyamine;
      (3) uridine 5'-diphosphoglucuronic acid; and
      (4) a selective residual esterase inhibitor, and
   (c) isolating hyoscyamine O-β-D-glucuronic acid.

13. A process, according to claim 12, wherein said selective residual esterase inhibitor is a competitive inhibitor of the esterases or a suicide substrate.

14. A process, according to claim 13, wherein said competitive inhibitor is lysine ethyl ester and said suicide substrate is phenylmethylsulfonyl fluoride.

* * * * *

UNITED STATES PATENT AND TRADEMARK OFFICE
CERTIFICATE OF CORRECTION

PATENT NO. : 4,518,691
DATED : May 21, 1985
INVENTOR(S) : Walter C. Herlihy

It is certified that error appears in the above-identified patent and that said Letters Patent are hereby corrected as shown below:

Column 4, line 42, that portion reading "fluroide" should read --fluoride--.

Column 5, lines 55-70, that portion reading

" 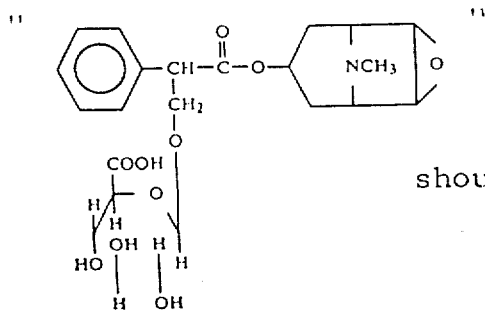 " should read -- 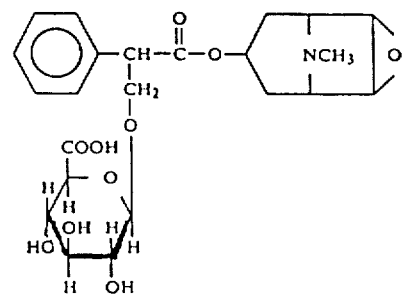 --.

UNITED STATES PATENT AND TRADEMARK OFFICE
CERTIFICATE OF CORRECTION

PATENT NO. : 4,518,691
DATED : May 21, 1985
INVENTOR(S) : Walter C. Herlihy

It is certified that error appears in the above-identified patent and that said Letters Patent are hereby corrected as shown below:

Column 6, lines 27-40, that portion reading

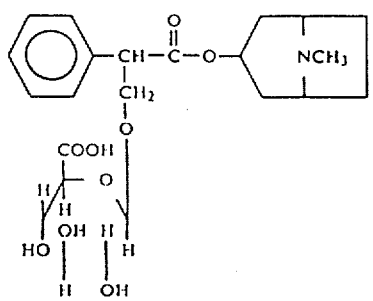      should read--      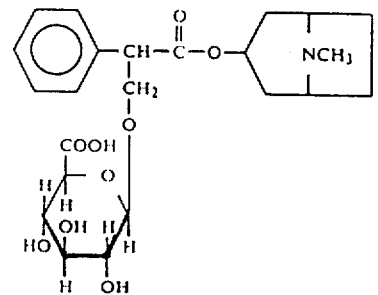      --.

Column 8, line 36, that portion reading "acid and" should read--acid; and--.

Signed and Sealed this

Eighth Day of October 1985

[SEAL]

Attest:

DONALD J. QUIGG

Attesting Officer

Commissioner of Patents and Trademarks—Designate